US008854611B2

(12) United States Patent
Benz et al.

(10) Patent No.: US 8,854,611 B2
(45) Date of Patent: Oct. 7, 2014

(54) METHOD FOR DETERMINING THE OPTIC CENTER OF A LENS BLANK

(71) Applicant: Benz Research and Development Corporation, Sarasota, FL (US)

(72) Inventors: Patrick H. Benz, Sarasota, FL (US); Andrew Larson, St. Paul, MN (US); Stephen E. Brauner, Bradenton, FL (US)

(73) Assignee: Benz Research and Development Corporation, Sarasota, FL (US)

( * ) Notice: Subject to any disclaimer, the term of this patent is extended or adjusted under 35 U.S.C. 154(b) by 163 days.

(21) Appl. No.: 13/660,670

(22) Filed: Oct. 25, 2012

(65) Prior Publication Data

US 2013/0107203 A1 May 2, 2013

Related U.S. Application Data

(60) Provisional application No. 61/552,247, filed on Oct. 27, 2011.

(51) Int. Cl.
*G01B 9/00* (2006.01)
*B24B 13/005* (2006.01)
*A61B 3/00* (2006.01)
*B24B 49/12* (2006.01)

(52) U.S. Cl.
CPC ............... *A61B 3/00* (2013.01); *B24B 13/0055* (2013.01); *B24B 49/12* (2013.01)
USPC ............................ 356/127; 356/124; 356/126

(58) Field of Classification Search
USPC ..................... 356/124–127, 239.1–239.8, 515
See application file for complete search history.

(56) References Cited

U.S. PATENT DOCUMENTS

| 4,656,590 | A | * | 4/1987 | Ace | ................................. 700/164 |
| 5,588,899 | A | * | 12/1996 | Gottschald | ......................... 451/5 |
| 6,100,971 | A | * | 8/2000 | Imaino et al. | .............. 356/237.2 |
| 7,533,453 | B2 | * | 5/2009 | Yancy | ............................... 29/557 |
| 7,980,920 | B2 | * | 7/2011 | Akiyama et al. | ................... 451/5 |

FOREIGN PATENT DOCUMENTS

| CA | 2323672 A1 | 4/2001 |
| WO | WO-03/018254 A2 | 3/2003 |

OTHER PUBLICATIONS

Banner Engineering Corp.: LED . . . I150-3 . . . Low-Angle LED Ring Lights (150 mm), Jun. 1, 2011, XP055055610, 2 pages.
International Search Report and Written Opinion; PCT/US2012/061968; Mar. 15, 2013, 13 pages.

* cited by examiner

*Primary Examiner* — Tarifur Chowdhury
*Assistant Examiner* — Jarreas C Underwood
(74) *Attorney, Agent, or Firm* — Foley & Lardner LLP

(57) ABSTRACT

A method comprises providing a lens blank, a precision positioning device, an illumination device, and a vision system, wherein the lens blank includes at least one feature whose position is known relative to a position of an optic center of the lens blank, and wherein the vision system comprises an image sensor and a processor; mounting the lens blank on the precision positioning device; illuminating the lens blank with the illumination device; viewing the lens blank with image sensor of the vision system; determining the position of the at least one feature using the processor; and determining the position of the optic center of the lens blank based on the position of the at least one feature using the processor.

74 Claims, 7 Drawing Sheets

FIG. 3
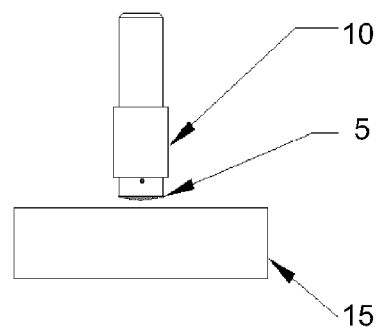
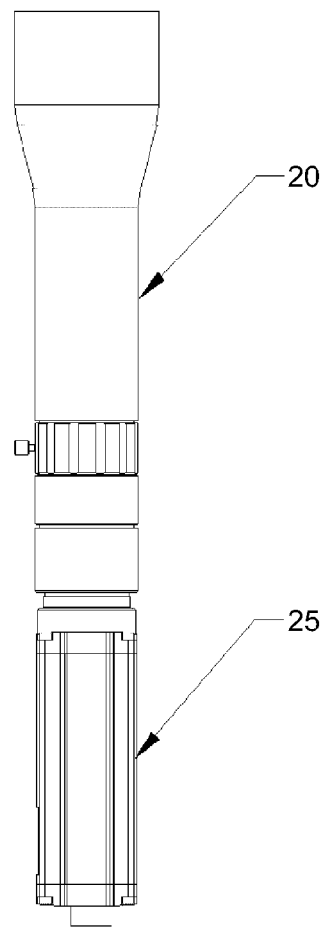

FIG. 4
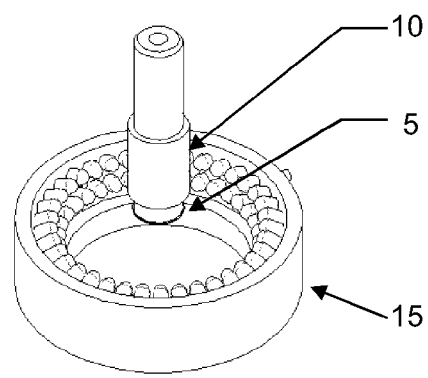
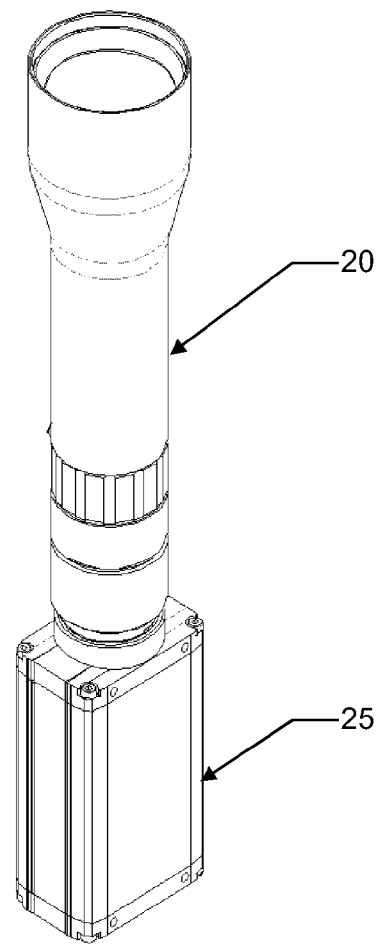

US 8,854,611 B2

METHOD FOR DETERMINING THE OPTIC CENTER OF A LENS BLANK

CROSS-REFERENCE TO RELATED APPLICATIONS

This application claims the benefit of U.S. Provisional Application No. 61/552,247, filed on Oct. 27, 2011, the contents of which are hereby incorporated by reference in their entirety into the present disclosure.

BACKGROUND OF THE INVENTION

This invention relates to a method for determining the optic center of a lens blank, such as an intraocular lens blank or a contact lens blank.

In the manufacture of lenses, the degree of accuracy of alignment of a lens blank to its fixture, e.g., a mandrel, determines the limit of concentricity possible through subsequent machining operations. The fixture is a device that holds the lens blank during multiple processing operations including blocking. A high degree of concentricity is advantageous in the manufacture of lenses since greater concentricity results in less prism. Prior methods of manufacturing lenses relied on mechanical centering for blocking the lens blank. However, mechanical blocking can be slow and inaccurate.

While some attempts have been made to automate this process to some extent, the prior art falls short of achieving the results of the present invention.

SUMMARY

In one embodiment, a method comprises providing a lens blank, a precision positioning device, an illumination device, and a vision system, wherein the lens blank includes at least one feature whose position is known relative to a position of an optic center of the lens blank, and wherein the vision system comprises an image sensor and a processor; mounting the lens blank on the precision positioning device; illuminating the lens blank with the illumination device; viewing the lens blank with image sensor of the vision system; determining the position of the at least one feature using the processor; and determining the position of the optic center of the lens blank based on the position of the at least one feature using the processor.

The method may further comprise transferring the lens blank to a fixture such that the optic center of the lens blank is aligned with a center of the fixture.

The method may further comprise determining, using the processor, a offset between the position of the optic center and a desired position of the optic center using the processor; and adjusting a position of the lens blank to the desired position based on the offset using the precision positioning device.

The vision system may further comprise an optical lens. The optical lens may be a telecentric lens.

The illumination device may be configured to illuminate the lens blank from sides of the lens blank. The illumination device may be a low angle ring lighting device. The illumination device may be a low angle red ring lighting device.

The at least one feature may be an edge of a raised or recessed portion of the lens blank. The at least one feature may be a step located at an outside diameter of the optic zone. The step may have a height between 20 and 100 microns. The at least one feature may be a circular feature, and the optic zone is located at a center of the circular feature. The at least one feature may be a feature that is molded, machined, or formed in the lens blank. The at least one feature may be a machined or molded edge of the lens blank.

The precision positioning system may comprise a pick head configured to hold the lens blank. The method may further comprise transferring the lens blank from the pick head to a centering nest; repositioning the pick head over the lens blank such that the optic center of the lens blank is aligned with a center of the pick head; and reattaching the pick head to the lens blank such that the optic center of the lens blank remains aligned with a center of the pick head. The pick head may be configured to hold the lens blank using a vacuum. The pick head may have a finish that does not interfere with the determination of the position of the at least one feature.

The method may further comprise automatically calibrating image sensor pixel size to a standard of predetermined dimension.

The lens blank may be an intraocular lens blank or a contact lens blank.

BRIEF DESCRIPTION OF THE DRAWINGS

The accompanying drawings, which are incorporated in and constitute a part of this specification, illustrate embodiments of the invention and together with the description serve to explain principles of the invention.

FIG. 3 is a front view of a system that can be used to perform the method of FIG. 1, including a pick head, a lens blank, an illumination device, and a vision system having an optical lens and an image sensor.

FIG. 4 is a front, top perspective view of the system of FIG. 3.

DETAILED DESCRIPTION OF THE PREFERRED EMBODIMENTS

Figure 1:
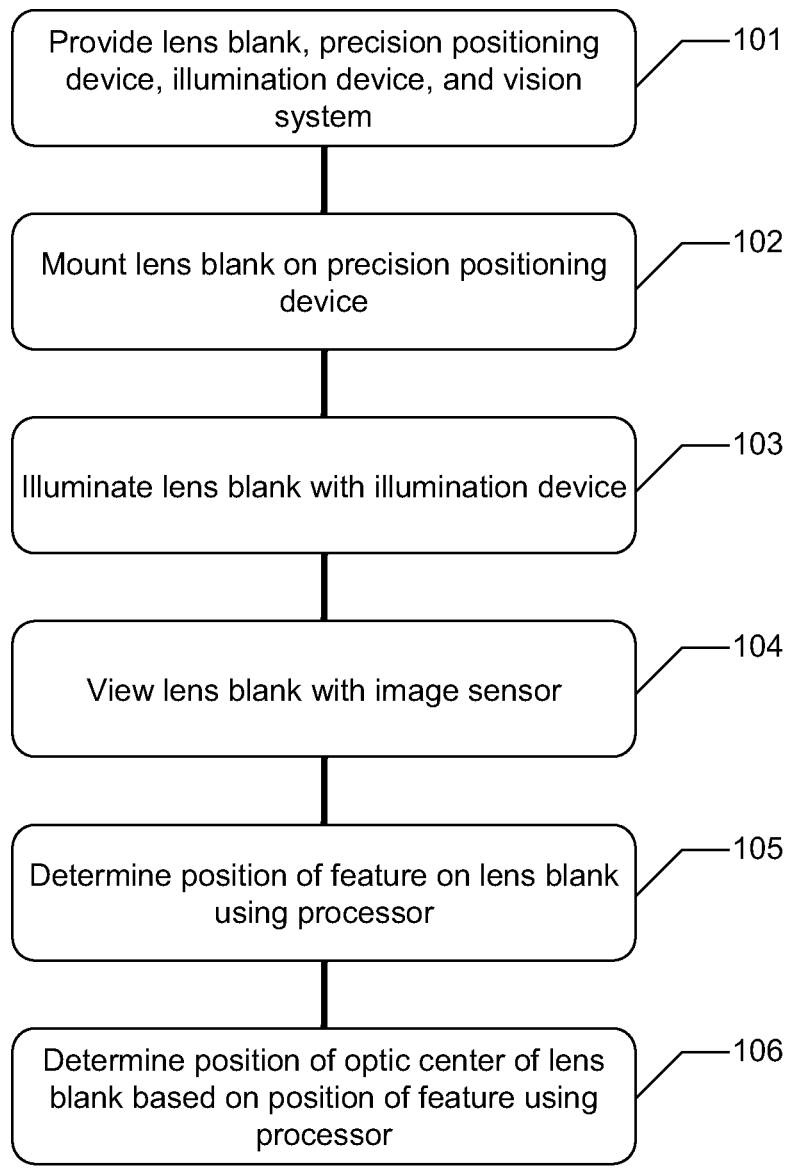
FIG. 1 is a flow chart for a method for determining the optic center of a lens blank according to one embodiment of the present invention.

The present invention relates to a method for determining the optic center of a lens blank, such as an intraocular lens blank or a contact lens blank. FIG. 1 is a flow chart showing the steps that may be used according to an embodiment of the invention. In a step 101, a lens blank, a precision positioning device, an illumination device, and a vision system are provided. The lens blank includes at least one feature whose position is known relative to a position of an optic center of the lens blank. The vision system comprises at least an image sensor and a processor. In a step 102, the lens blank is mounted on the precision positioning device. In a step 103, the lens blank is illuminated using the illumination device. In a step 104, the lens blank is viewed with the image sensor. In a step 105, the processor is used to determine the position of the feature on the lens blank. In a step 106, the processor is used to determine the position of the optic center of the lens blank based on the determined position of the feature. After the position of the optic center is determined, the processor may be used to determine the offset between the position of the optic center and the desired position of the optic center. The processor may transfer this information to a precision positioning system, which can then be used to position the lens blank in the desired position based on the offset. For example, the lens blank may be transferred to a fixture, such as a mandrel, such that the optic center of the lens blank is aligned with the center of the fixture.

Figure 2:
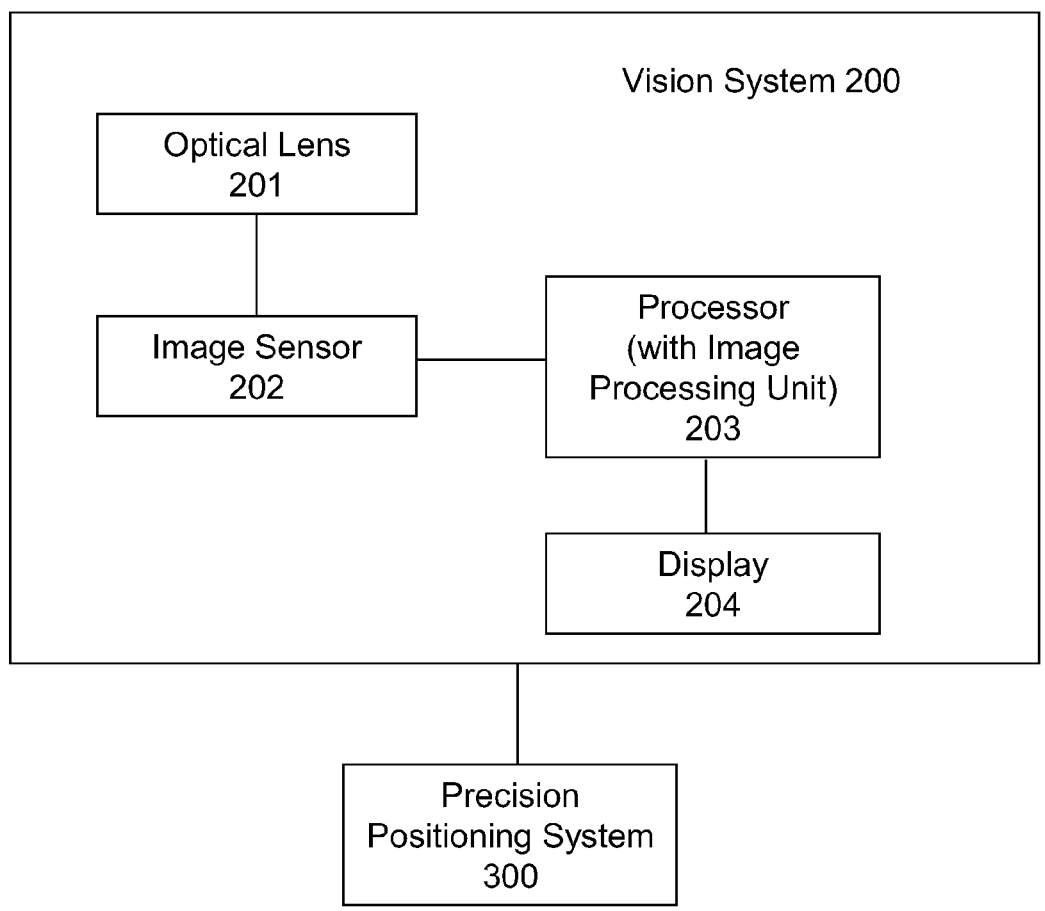
FIG. 2 is a block diagram of system including a vision system and a precision positioning system according to embodiments of the present invention.

FIG. 2 is a block diagram of system according to embodiments of the present invention. The vision system 200 may include an optical lens 201, which is may be used to focus on the lens blank. The vision system 200 further includes an image sensor 202, such as a camera. The image sensor 202 is used to obtain images of the lens blank. The vision system further includes a processor 203. The processor includes an image processing unit, such that the processor 203 may process images obtained from the image sensor 202. Generally, the processor is programmed to find and return information of interest. For example, the processor may be configured to differentiate the feature or features on the lens blank from the remainder of the lens blank. The processor 203 may thus automatically determine the location of the feature or features on the lens blank. Then, the processor 203 may determine the location of the optic center of the lens blank based on the position of the feature or features. An example of a processor that may be used is the Impact M40 M-Series Processor, available from PPT Vision, Inc.

Figure 7A:
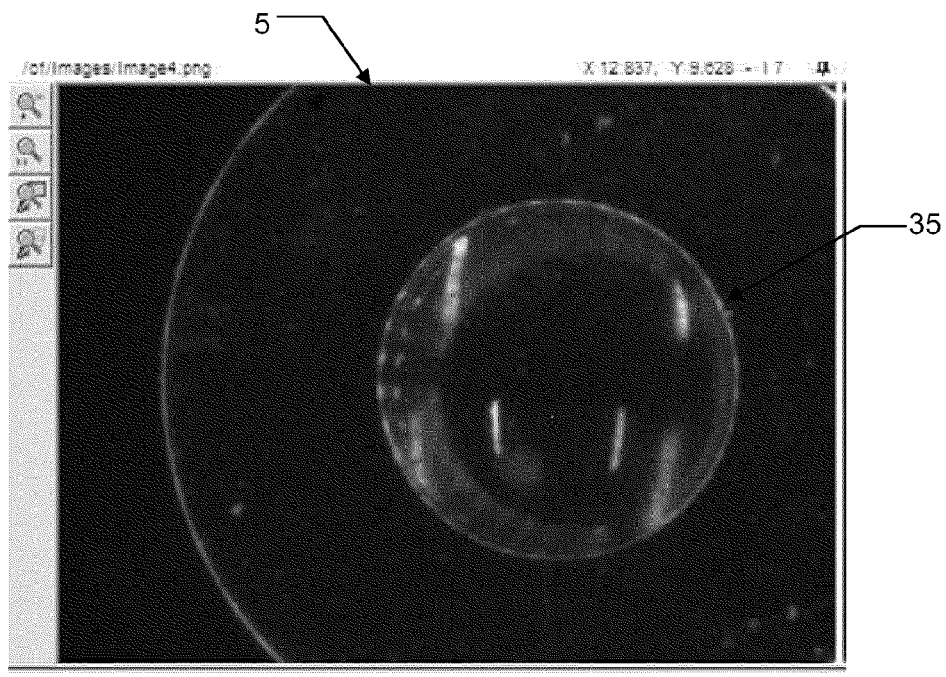
FIGS. 7A and 7B show a lens blank as captured by an image sensor and viewed on a computer monitor, both before and after a vision system processor recognizes a feature on the lens blank and determines an optic center of the lens blank.
Figure 7B:
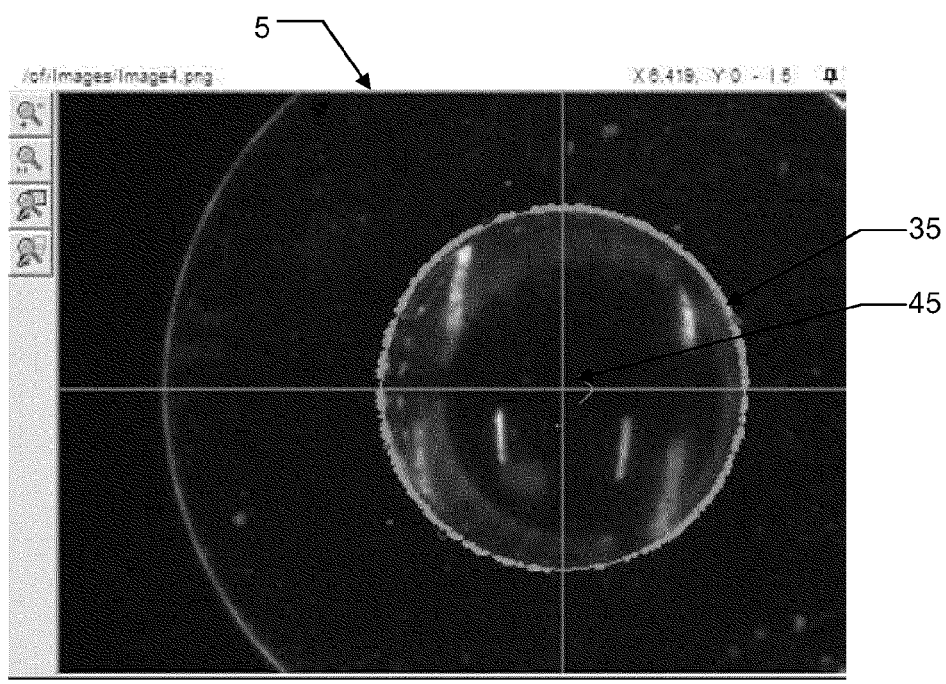

The vision system 200 may further include a display 204 that shows the image obtained from the image sensor 202, as shown in FIG. 7A. The display may also show a representation of the feature or features that have been identified by the processor and a representation of the optic center of the lens blank, as shown in FIG. 7B. For example, the processor 203 may be configured to highlight the identified location of the feature or features on the display 204. The processor 203 may be configured to indicate the optic center of the lens blank using intersecting lines, where the intersection point of the lines represents the optic center of the lens blank. In one embodiment, the processor may be configured to automatically calibrate image sensor pixel size to a standard of predetermined dimension. The processor 203 of the vision system 200 is operably connected to the precision positioning system 300, such that the processor 203 can provide information to the precision positioning system 300, which can adjust the position of the lens blank. Thus, the entire process can be automated such that it requires little or no human input.

Figure 5:
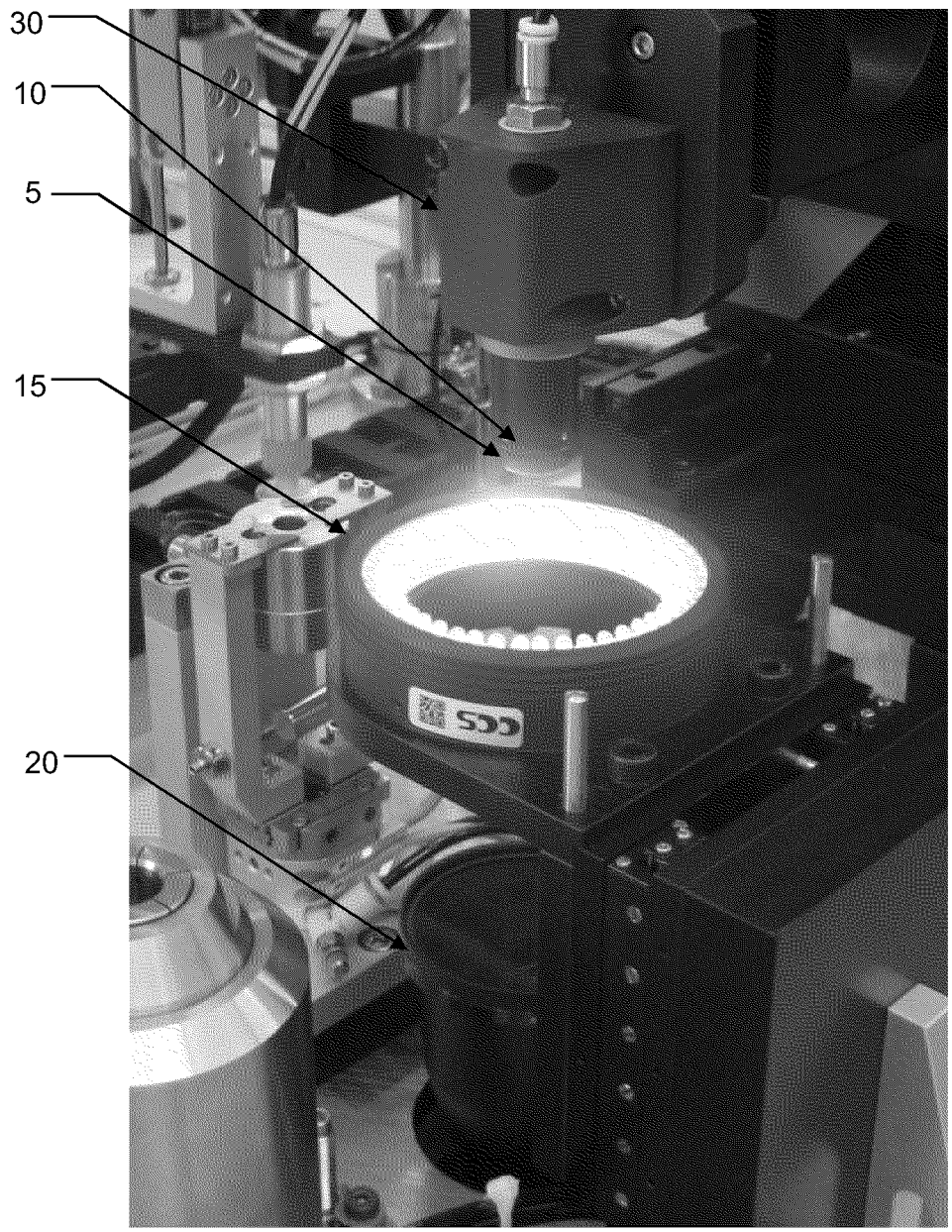
FIG. 5 is an image depicting the system of FIG. 3, which also shows a precision positioning device.

FIGS. 3-5 are views of a system that can be used to perform the method of embodiments of the present invention. The system may include a pick head 10 configured to hold the lens blank 5 while the optic center of the lens blank is determined. The pick head 10 may hold the lens blank 5 using any known devices. For example, the pick head 10 may hold the lens blank 5 using a vacuum device, so as not to distort the lens blank 5. The pick head W may have a finish that does not interfere with the ability of an image sensor to find a feature on the lens blank 5.

When the lens blank is initially picked by the pick head it may not yet be accurately centered to the pick head. Because of a 5 degree haptic angle, 5 degree angle on the pick head, and 5 degree angle on the mandrel mounting surface, it can be important for the lens blank to be centered on the pick head. If they are not on center, the lens blank may be blocked at a different elevations around its perimeter. This problem may be resolved by finding the center of the lens blank optic zone with the vision system and then placing the lens onto a centering nest. A vacuum may be used to hold the lens blank to the centering nest while the pick head vacuum is released and the pick head separated from the lens blank. Once separated from the lens blank, the pick head is repositioned over the center of the lens blank based on the measured offset and moved onto the lens blank. Vacuum in the pick head is turned on again and centering nest vacuum is released. By doing this, the lens blank is centered on the pick head.

The pick head is a part of a precision positioning system 30, as shown in FIG. 5. The precision positioning system 30 may be any system that is capable of moving the lens blank to a desired position. The precision positioning system preferably has a uni-directional repeatability of at least +25 nm and a bi-directional repeatability of at least +100 nm. An example of such a system is the ANT130-XY Series Two-Axis, Crossed-Roller Bearing Linear Stage, available from Aerotech, Inc.

An illumination device 15 illuminates the lens blank during the process. The illumination device may be any lighting device that increases the contrast between the feature or features on the lens blank 5 and the remainder of the lens blank 5. For example, the illumination device 15 may be a low angle ring lighting device, as shown in FIGS. 4 and 5. The low angle ring light device may emit red light. When the lens blank 5 is mounted on a vertical pick head 10, the ring light may be disposed slightly below the lens blank 5, so as to illuminate the lens blank 5 from a location under and to the sides of the lens blank 5, as shown in FIGS. 3-5.

The system further includes an optical lens 20, which may be used to focus on the lens blank 5. The optical lens 20 may be a telecentric optical lens. For example, the optical lens 20 may have a maximum sensor format of 0.5 in., a working distance of 103±3 mm, a resolution (image space @ F10) of greater than 40% at 40 lp/mm, a telecentricity of less than 0.1°, a maximum distortion of less than 0.3%, a DOF (10%@20 l/mm) of ±1.4 mm at F10, an F6 aperature (closed), and a broadband antireflection coating on the lens element (425-675 nm). An example of such an optical lens is the Techspec® Silver Series Telecentric Lens Model #63-074, available from Edmund Optics Inc.

The system further includes an image sensor 25, such as a camera. The camera may be attached to the optical lens 20, as shown in FIGS. 3 and 4. The camera may use a progressive scan CCD pick-up device (1628 (H)×1236 (V) pixels). The camera may have a sensor size of 1/1.8 in. (8.923 mm) diag., (7.04 mm (H)×5.28 mm (V)). The camera may have a capture rate of 14 full-resolution fps, a pixel size of 4.4×4.4 microns, a gain of 100% to 1023%, a shutter open time of 31 to 1,000,000 μsec, and an exposure start delay of 58.92 μsec. The camera may use a 24 VDC power supply provided by a camera cable (3.4 watts). An example of such a camera is the M290 M-Series Camera, available from PPT Vision, Inc. When the lens blank 5 is mounted on a vertical pick head 10, the optical lens and image sensor may be disposed so as to look upwards at the lens blank 5, as shown in FIGS. 3-5.

Figure 6A:
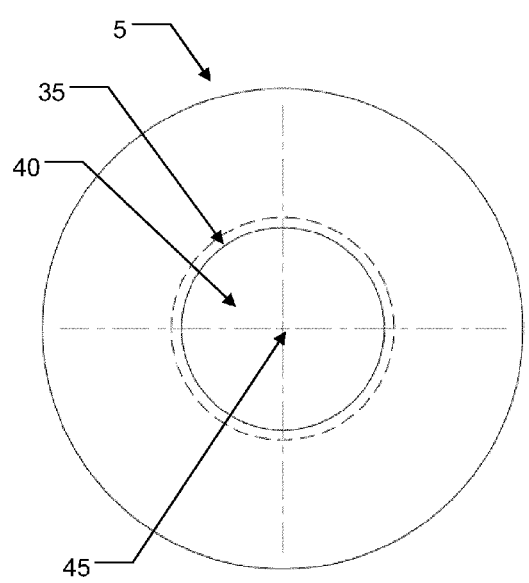
FIGS. 6A and 6B are front and side views of a lens blank that can be used in embodiments of the present invention.
Figure 6B:
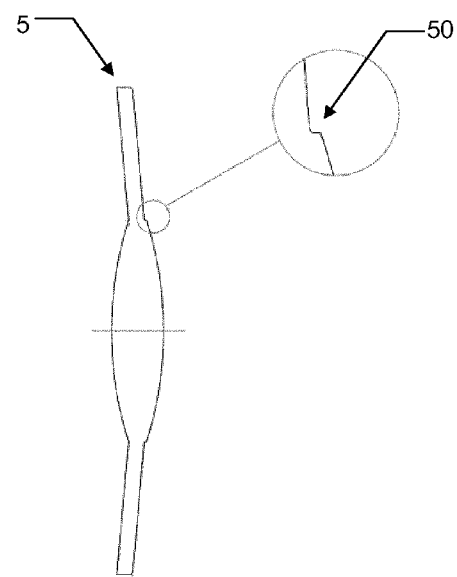

FIGS. 6A and 6B show an example of a lens blank 5 that can be used in embodiments of the present invention. As described above, the lens blank 5 has at least one feature that can be identified by the vision system. The feature 35 may be an edge of a raised or recessed portion of the lens blank. The feature may be a circular feature. In the lens blank of FIGS. 6A and 6B, for example, the feature 35 is a circular step 50 located at the outside diameter of the optic zone 40. In this case, the optic center 45 is located at the center of the optic zone 40. The 50 step may have a height between 20 and 100 microns, for example. The feature may be a feature that is molded, machined, or otherwise formed in the lens blank 5. While FIGS. 6A and 6B show one example of a feature that can be identified by the processor of the vision system, the feature is not limited to the type depicted. For example, the feature may be a rib that extends above a haptic and is concentric to the optic zone, a groove in a haptic that is concentric to the optic zone, a series of raised dots or dimples, or a pattern of holes. The feature may be a machined or molded edge of the lens blank. The feature can be any feature of the lens blank 5 that can be viewed with the image sensor 25 and identified by the processor, and whose position is known relative to the optic center of the lens blank 5.

The present invention is not limited to the embodiments disclosed above. Those embodiments, however, disclose examples of configurations that can advantageously determine the optic center of a lens blank, such as an intraocular lens blank or a contact lens blank. The present invention can be implemented in a wide variety of configurations beyond those disclosed herein. Other embodiments of the invention will be apparent to those skilled in the art from consideration of the specification and practice of the invention disclosed herein. It is intended that the specification and examples be considered as exemplary only.

What is claimed is:

1. A method comprising:
providing a lens blank, a precision positioning device, an illumination device, and a vision system, wherein the lens blank includes at least one feature whose position is known relative to a position of an optic center of the lens blank, and wherein the vision system comprises an image sensor and a processor;
mounting the lens blank on the precision positioning device;
illuminating the lens blank with the illumination device;
viewing the lens blank with image sensor of the vision system;
determining the position of the at least one feature using the processor; and
determining the position of the optic center of the lens blank based on the position of the at least one feature using the processor,
wherein the at least one feature is a circular feature, and the optic zone is located at a center of the circular feature.

2. The method of claim 1, further comprising transferring the lens blank to a fixture such that the optic center of the lens blank is aligned with a center of the fixture.

3. The method of claim 1, further comprising:
determining an offset between the position of the optic center and a desired position of the optic center using the processor; and
adjusting a position of the lens blank to the desired position based on the offset using the precision positioning device.

4. The method of claim 1, wherein the vision system further comprises an optical lens.

5. The method of claim 4, wherein the optical lens is a telecentric lens.

6. The method of claim 1, wherein the illumination device is configured to illuminate the lens blank from sides of the lens blank.

7. The method of claim 1, wherein the illumination device is a low angle ring lighting device.

8. The method of claim 7, wherein the illumination device is a low angle red ring lighting device.

9. The method of claim 1, wherein the at least one feature is an edge of a raised or recessed portion of the lens blank.

10. The method of claim 1, wherein the at least one feature is a step located at an outside diameter of the optic zone.

11. The method of claim 10, wherein the step has a height between 20 and 100 microns.

12. The method of claim 1, wherein the at least one feature is a feature that is molded, machined, or formed in the lens blank.

13. The method of claim 1, wherein the at least one feature is a machined or molded edge of the lens blank.

14. The method of claim 1, wherein the precision positioning system comprises a pick head configured to hold the lens blank.

15. The method of claim 14, further comprising:
transferring the lens blank from the pick head to a centering nest;
repositioning the pick head over the lens blank such that the optic center of the lens blank is aligned with a center of the pick head; and
reattaching the pick head to the lens blank such that the optic center of the lens blank remains aligned with a center of the pick head.

16. The method of claim 14, wherein the pick head is configured to hold the lens blank using a vacuum.

17. The method of claim 14, wherein the pick head has a finish that does not interfere with the determination of the position of the at least one feature.

18. The method of claim 1, further comprising automatically calibrating image sensor pixel size to a standard of predetermined dimension.

19. The method of claim 1, wherein the lens blank is an intraocular lens blank or a contact lens blank.

20. A method comprising:
providing a lens blank, a precision positioning device, an illumination device, and a vision system, wherein the lens blank includes at least one feature whose position is known relative to a position of an optic center of the lens blank, and wherein the vision system comprises an image sensor and a processor;
mounting the lens blank on the precision positioning device;
illuminating the lens blank with the illumination device;
viewing the lens blank with image sensor of the vision system;
determining the position of the at least one feature using the processor; and
determining the position of the optic center of the lens blank based on the position of the at least one feature using the processor,
wherein the illumination device is configured to illuminate the lens blank from sides of the lens blank.

21. The method of claim 20, further comprising transferring the lens blank to a fixture such that the optic center of the lens blank is aligned with a center of the fixture.

22. The method of claim 20, further comprising:
determining an offset between the position of the optic center and a desired position of the optic center using the processor; and
adjusting a position of the lens blank to the desired position based on the offset using the precision positioning device.

23. The method of claim 20, wherein the vision system further comprises an optical lens.

24. The method of claim 23, wherein the optical lens is a telecentric lens.

25. The method of claim 20, wherein the illumination device is a low angle ring lighting device.

26. The method of claim 25, wherein the illumination device is a low angle red ring lighting device.

27. The method of claim 20, wherein the at least one feature is an edge of a raised or recessed portion of the lens blank.

28. The method of claim 20, wherein the at least one feature is a step located at an outside diameter of the optic zone.

29. The method of claim 28, wherein the step has a height between 20 and 100 microns.

30. The method of claim 20, wherein the at least one feature is a circular feature, and the optic zone is located at a center of the circular feature.

31. The method of claim 20, wherein the at least one feature is a feature that is molded, machined, or formed in the lens blank.

32. The method of claim 20, wherein the at least one feature is a machined or molded edge of the lens blank.

33. The method of claim 20, wherein the precision positioning system comprises a pick head configured to hold the lens blank.

34. The method of claim 33, further comprising:
transferring the lens blank from the pick head to a centering nest;
repositioning the pick head over the lens blank such that the optic center of the lens blank is aligned with a center of the pick head; and
reattaching the pick head to the lens blank such that the optic center of the lens blank remains aligned with a center of the pick head.

35. The method of claim 33, wherein the pick head is configured to hold the lens blank using a vacuum.

36. The method of claim 33, wherein the pick head has a finish that does not interfere with the determination of the position of the at least one feature.

37. The method of claim 20, further comprising automatically calibrating image sensor pixel size to a standard of predetermined dimension.

38. The method of claim 20, wherein the lens blank is an intraocular lens blank or a contact lens blank.

39. A method comprising:
providing a lens blank, a precision positioning device, an illumination device, and a vision system, wherein the lens blank includes at least one feature whose position is known relative to a position of an optic center of the lens blank, and wherein the vision system comprises an image sensor and a processor;
mounting the lens blank on the precision positioning device;
illuminating the lens blank with the illumination device;
viewing the lens blank with image sensor of the vision system;
determining the position of the at least one feature using the processor; and
determining the position of the optic center of the lens blank based on the position of the at least one feature using the processor,
wherein the illumination device is a low angle ring lighting device.

40. The method of claim 39, further comprising transferring the lens blank to a fixture such that the optic center of the lens blank is aligned with a center of the fixture.

41. The method of claim 39, further comprising:
determining an offset between the position of the optic center and a desired position of the optic center using the processor; and
adjusting a position of the lens blank to the desired position based on the offset using the precision positioning device.

42. The method of claim 39, wherein the vision system further comprises an optical lens.

43. The method of claim 42, wherein the optical lens is a telecentric lens.

44. The method of claim 39, wherein the illumination device is configured to illuminate the lens blank from sides of the lens blank.

45. The method of claim 39, wherein the illumination device is a low angle red ring lighting device.

46. The method of claim 39, wherein the at least one feature is an edge of a raised or recessed portion of the lens blank.

47. The method of claim 39, wherein the at least one feature is a step located at an outside diameter of the optic zone.

48. The method of claim 47, wherein the step has a height between 20 and 100 microns.

49. The method of claim 39, wherein the at least one feature is a circular feature, and the optic zone is located at a center of the circular feature.

50. The method of claim 39, wherein the at least one feature is a feature that is molded, machined, or formed in the lens blank.

51. The method of claim 39, wherein the at least one feature is a machined or molded edge of the lens blank.

52. The method of claim 39, wherein the precision positioning system comprises a pick head configured to hold the lens blank.

53. The method of claim 52, further comprising:
transferring the lens blank from the pick head to a centering nest;
repositioning the pick head over the lens blank such that the optic center of the lens blank is aligned with a center of the pick head; and
reattaching the pick head to the lens blank such that the optic center of the lens blank remains aligned with a center of the pick head.

54. The method of claim 52, wherein the pick head is configured to hold the lens blank using a vacuum.

55. The method of claim 52, wherein the pick head has a finish that does not interfere with the determination of the position of the at least one feature.

56. The method of claim 39, further comprising automatically calibrating image sensor pixel size to a standard of predetermined dimension.

57. The method of claim 39, wherein the lens blank is an intraocular lens blank or a contact lens blank.

58. A method comprising:
providing a lens blank, a precision positioning device, an illumination device, and a vision system, wherein the lens blank includes at least one feature whose position is known relative to a position of an optic center of the lens blank, and wherein the vision system comprises an image sensor and a processor;
mounting the lens blank on the precision positioning device;
illuminating the lens blank with the illumination device;
viewing the lens blank with image sensor of the vision system;
determining the position of the at least one feature using the processor; and
determining the position of the optic center of the lens blank based on the position of the at least one feature using the processor,
wherein the at least one feature is a step located at an outside diameter of the optic zone.

59. The method of claim 58, further comprising transferring the lens blank to a fixture such that the optic center of the lens blank is aligned with a center of the fixture.

60. The method of claim 58, further comprising:
  determining an offset between the position of the optic center and a desired position of the optic center using the processor; and
  adjusting a position of the lens blank to the desired position based on the offset using the precision positioning device.

61. The method of claim 58, wherein the vision system further comprises an optical lens.

62. The method of claim 61, wherein the optical lens is a telecentric lens.

63. The method of claim 58, wherein the illumination device is configured to illuminate the lens blank from sides of the lens blank.

64. The method of claim 58, wherein the illumination device is a low angle ring lighting device.

65. The method of claim 64, wherein the illumination device is a low angle red ring lighting device.

66. The method of claim 58, wherein the step has a height between 20 and 100 microns.

67. The method of claim 58, wherein the at least one feature is a circular feature, and the optic zone is located at a center of the circular feature.

68. The method of claim 58, wherein the at least one feature is a feature that is molded, machined, or formed in the lens blank.

69. The method of claim 58, wherein the precision positioning system comprises a pick head configured to hold the lens blank.

70. The method of claim 69, further comprising:
  transferring the lens blank from the pick head to a centering nest;
  repositioning the pick head over the lens blank such that the optic center of the lens blank is aligned with a center of the pick head; and
  reattaching the pick head to the lens blank such that the optic center of the lens blank remains aligned with a center of the pick head.

71. The method of claim 69, wherein the pick head is configured to hold the lens blank using a vacuum.

72. The method of claim 69, wherein the pick head has a finish that does not interfere with the determination of the position of the at least one feature.

73. The method of claim 58, further comprising automatically calibrating image sensor pixel size to a standard of predetermined dimension.

74. The method of claim 58, wherein the lens blank is an intraocular lens blank or a contact lens blank.

* * * * *